United States Patent
Stein et al.

(10) Patent No.: US 9,072,664 B2
(45) Date of Patent: Jul. 7, 2015

(54) PROCESS FOR MANUFACTURING FLOWABLE POWDER DRUG COMPOSITIONS

(75) Inventors: Stephen W. Stein, Lino Lakes, MN (US); Michael W. Mueting, Stillwater, MN (US); Timothy D. Dunbar, Woodbury, MN (US)

(73) Assignee: 3M INNOVATIVE PROPERTIES COMPANY, St. Paul, MN (US)

(*) Notice: Subject to any disclaimer, the term of this patent is extended or adjusted under 35 U.S.C. 154(b) by 292 days.

(21) Appl. No.: 12/992,633

(22) PCT Filed: Apr. 17, 2009

(86) PCT No.: PCT/US2009/040892
§ 371 (c)(1),
(2), (4) Date: Nov. 15, 2010

(87) PCT Pub. No.: WO2009/142852
PCT Pub. Date: Nov. 26, 2009

(65) Prior Publication Data
US 2011/0064867 A1 Mar. 17, 2011

Related U.S. Application Data

(60) Provisional application No. 61/055,340, filed on May 22, 2008.

(51) Int. Cl.
*B05D 3/00* (2006.01)
*A61K 9/00* (2006.01)

(52) U.S. Cl.
CPC .................................. *A61K 9/0075* (2013.01)

(58) Field of Classification Search
CPC ....................................................... B05D 3/00
USPC ........................... 427/2.14; 514/769; 524/354
See application file for complete search history.

(56) References Cited

U.S. PATENT DOCUMENTS

| | | | |
|---|---|---|---|
| 2,801,185 | A | 7/1957 | Iler |
| 4,455,205 | A | 6/1984 | Olson et al. |
| 4,478,876 | A | 10/1984 | Chung |
| 4,486,504 | A | 12/1984 | Chung |
| 4,491,508 | A | 1/1985 | Olson et al. |
| 4,522,958 | A | 6/1985 | Das et al. |
| 5,037,579 | A | 8/1991 | Matchett |
| 5,258,225 | A | 11/1993 | Katsamberis |
| 5,443,603 | A | 8/1995 | Kirkendall |
| 5,858,410 | A | 1/1999 | Muller et al. |
| 6,051,252 | A | 4/2000 | Liebowitz et al. |
| 6,153,224 | A | 11/2000 | Staniforth |
| 6,329,058 | B1 | 12/2001 | Arney et al. |
| 6,432,526 | B1 | 8/2002 | Arney et al. |
| 6,811,096 | B2 * | 11/2004 | Frazier et al. ................. 239/398 |
| 7,189,768 | B2 | 3/2007 | Baran, Jr. et al. |
| 8,348,605 | B2 * | 1/2013 | de Broqueville ............. 415/203 |
| 2003/0102099 | A1 | 6/2003 | Yadav et al. |
| 2005/0113489 | A1 | 5/2005 | Baran, Jr. et al. |
| 2005/0196345 | A1 | 9/2005 | Diederichs et al. |
| 2005/0238804 | A1 | 10/2005 | Garbar et al. |
| 2007/0020197 | A1 * | 1/2007 | Galli et al. ........................ 424/46 |
| 2007/0212542 | A1 | 9/2007 | Guo et al. |
| 2010/0266697 | A1 | 10/2010 | Dunbar |
| 2013/0177649 | A1 * | 7/2013 | Van Gessel ................... 424/490 |

FOREIGN PATENT DOCUMENTS

| | | |
|---|---|---|
| WO | WO 02/00197 | 1/2002 |
| WO | WO 02/43700 | 6/2002 |
| WO | WO 2007/019229 | 2/2007 |
| WO | WO 2007019229 A1 * | 2/2007 |
| WO | WO 2007/117661 | 10/2007 |
| WO | WO 2007/125159 A1 | 11/2007 |
| WO | WO 2008/002568 | 1/2008 |
| WO | WO 2008/0055951 A1 | 5/2008 |
| WO | WO 2009/142852 | 11/2009 |

OTHER PUBLICATIONS

Teunou et al., Batch and continuous fluid bed coating—review and state of the art, Journal of Food Engineering 53 (2002) 325-340.*
Linsenbuhler, M., et al., "An innovative dry powder coating process in non-polar liquids producing tailor-made miro-particles," *Powder Technology*, 158, 2003, pp. 3-20.
Kawashima, Y., et al., Design of inhalation dry powder of pranlukast hydrate to improve dispersibility by the surface modification with light anhydrous silicic acid (AEROSIL 200), *Int'l Journal of Pharmaceutics*, 173, 1998, pp. 243-251.
Li, J. et al., "Visualization and Characterization of Poly(amidoamine) Dendrimers by Atomic Force Microscopy," *Langmuir 2000*, 5613-5616.
Sastre et al., "On the Incorporation of Buckminsterfullerene $C_{6C}$ in the Supercages of Zeolite Y," *J. Phys. Chem.* B 1997, 101, 10184-10190.
Binks, B.P. et al., "Phase Inversion of particle-stabilized materials from foams to dry water," *Nature Materials*, vol. 5, Nov. 2006, 865-869.
Ben-Jebria, et al.; "Inhalation System for Pulmonary Aerosol Drug Delivery in Rodents Using Large Porous Particles"; Aerosol Science and Technology; vol. 32, No. 5; 2000; pp. 421-433.
Extended European Search Report dated Apr. 17, 2013 for related EP Application No. 09751082.0; 4 pgs.

* cited by examiner

*Primary Examiner* — Dah-Wei D Yuan
*Assistant Examiner* — Hai Yan Zhang
(74) *Attorney, Agent, or Firm* — Colene H. Blank

(57) ABSTRACT

Powder drug compositions exhibiting improved flow properties are manufactured by spraying a suspension of surface-modified nanoparticles having an average particle size diameter of less than 100 nm in a dryable liquid carrier onto particles of a powder ingredient of a drug composition. The liquid carrier is rapidly dried so as to leave the nanoparticles on the powder. Other ingredients of the powder drug composition can also be added.

18 Claims, No Drawings

PROCESS FOR MANUFACTURING FLOWABLE POWDER DRUG COMPOSITIONS

CROSS REFERENCE TO RELATED APPLICATIONS

This application is a national stage filing under 35 U.S.C. 371 of PCT/US2009/040892, filed Apr. 17, 2009, which claims priority to U.S. Provisional Application No. 61/055,340, filed Apr. 17, 2009, the disclosure of which is incorporated by reference in its/their entirety herein.

FIELD

The invention relates generally to manufacturing powder drug compositions including surface-modified nanoparticles to improve flowability.

BACKGROUND

The handling, mixing and delivery of bulk solids present unique difficulties when the solids are handled in powdered form. Often, one or more physical properties of the powdered particulates themselves are important, or even critical, to the application for which the composition is intended. Particulate shape, particulate size and particulate porosity often describe important physical properties or characteristics. Environmental conditions (humidity, temperature, shear forces among others) encountered by a powder during use or storage can and often do affect one or more properties of the particulates. Aggregation, agglomeration, attrition and flocculation represent the most common degradative effects on a powder and their presence or progression greatly limits the utility and viability of many powder compositions.

Achieving a uniform blend of dry bulk solids is a problem faced daily by engineers and operators in industries as varied as pharmaceuticals, foods, plastics and battery production. Even when an acceptable blend is obtained additional challenges arise in maintaining the blend through one or more pieces of downstream equipment. Poor blending or the inability to maintain an adequate blend before and during processing lead to additional and unnecessary costs, including costs associated with rejected material and decreased yields, added blending time and energy, decreased productivities, start-up delays and defective or out-of-specification products. Powder caking of raw and in-process materials, particularly during storage (in, e.g., bags or drums) can also pose significant problems. Both powder caking and an inability to achieve uniform blends and mixtures can decrease batch uniformity which, among other drawbacks, can require increased testing and sampling. In pharmaceutical applications, batch disuniformities translate directly to dose disuniformities.

Some flowability aids are known. Fumed silica, for example, is one popular powder additive that can be used to improve flow characteristics. While relatively inexpensive, fumed silica often is ineffective in preventing agglomeration of many particle types. Flowability is also a matter of degree; many, if not most, uses of fumed silica lead to some agglomeration and aggregation. Some undemanding industrial applications can tolerate a level of agglomeration not tolerated in more demanding applications. Applications involving precise metering or mixing of a powder, however, require more. Even in relatively undemanding applications the ability to improve powder flow can provide an increase in homogeneity with milder mixing conditions or with reduced mixing periods. Additionally, increased powder flowabilities can allow utilization of lower levels of expensive ingredients, e.g., dyes and pigments, particularly where the required level of such ingredients correlates with the dispersibility of the materials in the powder with which they are mixed.

The preparation or delivery of pharmaceutical drugs and medicaments as powders is particularly demanding. Pharmaceutical applications must take careful account of various particle or powder characteristics, and pharmaceutical compositions often are prepared as powders as an intermediate step to final formulation in myriad forms for delivery to the patient. Pharmaceutical compositions can be tabletted or encapsulated for oral gastro-intestinal ingestion and delivery. They also can be incorporated into a dry powder inhaler (DPI) for delivery to the respiratory tract. The ability to achieve homogeneous blends of compositions containing relatively low levels (by weight) of pharmaceutically active ingredients is very difficult.

Recent advances in improving the flowability characteristics of powders by adding surface-modified nanoparticles are disclosed in International Publication WO 2007/019229, entitled "Compositions Exhibiting Improved Flowability" (incorporated herein by reference). However, there are significant challenges in handling surface-modified nanoparticles and in manufacturing powder formulations, such as medicament powder formulations, having surface-modified nanoparticles therein.

SUMMARY

It has now been found that surface-modified nanoparticles can be beneficially applied to a powder drug formulation by spraying the nanoparticles suspended in a dryable liquid carrier on to the powder and drying off the liquid. This is useful for many powder compositions, but especially useful for ingredients in a powder drug formulation to avoid prolonged contact with the dryable liquid, which can cause unwanted physical and/or chemical changes to the powder (e.g., crystal growth).

Accordingly, one aspect of the invention provides a process for manufacturing a highly flowable and/or floodable powder drug composition, including the steps of preparing a suspension of surface-modified nanoparticles having an average particle size diameter of less than 100 nm in a dryable liquid carrier, spraying the dryable liquid carrier containing nanoparticles onto particles of a powder ingredient of a drug composition, evaporating off the dryable liquid carrier so as to leave the nanoparticles on the powder without the dryable liquid carrier (i.e., substantially free of the liquid, although trace residues could be present), and optionally adding other ingredients of the powder drug composition. The resulting powder drug composition is highly flowable and/or floodable. It should also be noted that the invention described herein is also beneficial and can be used for any powder composition to improve flowability and/or floodability of the powder.

The surface-modified nanoparticles may have a hydrophilic or hydrophobic surface modification. Examples of core materials for the nanoparticles include silicas, calcium phosphates, iron oxides, zinc oxides, zirconia and alumina compounds. The average diameter of the nanoparticles may be less than 20 nm.

Examples of the dryable liquid carrier include water, isopropyl alcohol, ethanol, dimethyl ether, heptane, toluene, liquefied carbon dioxide, liquefied hydrocarbon, liquefied hydrofluorocarbon, and mixtures thereof.

The particles of the powder drug composition generally have a median particle size diameter less than 200 micrometers. The diameter of the powder will, however, be substantially larger than the diameter of the nanoparticles (usually 10 to 1000 times larger).

In one aspect of the invention the powder drug composition is a powdered medicament formulation, for example a dry powder inhaler formulation. The powder ingredient of the drug composition or medicament formulation may comprise lactose (for example, used as part of a dry powder inhaler formulation).

The particles of the powder drug composition may be stirred (i.e., agitated in some way) as the dryable liquid carrier containing nanoparticles is sprayed onto the particles. The liquid may be removed by vacuum filtration, spray drying, rotary evaporation, bulk evaporation or freeze drying. For example, the particles of the powder drug composition may form a bed of particles on a filtration media through which a suction is applied to the bed of particles. Alternatively, the particles of the powder ingredient may be airborne when the dryable liquid carrier containing nanoparticles is sprayed onto the surface of the powder ingredient. For example, the particles of the powder ingredient may be contained in one airflow that impinges upon a second airflow containing droplets of the dryable liquid carrier containing nanoparticles.

DETAILED DESCRIPTION

The use of surface-modified nanoparticles to improve the flowability/floodability of powders raises unique challenges in terms of manufacturing for a number of reasons. For example, due to their extremely small size, handling the nanoparticles can be difficult and it is helpful to suspend them in a suitable liquid carrier, which can then be mixed with the powder material to which the nanoparticles are to be applied, such as a drug or component of a drug formulation. However, this requires chemical and physical compatibility of the liquid carrier with both the powder and the nanoparticles, which is often not the case. The liquid carrier may, for example, partially solubilize the powder, or it may cause chemical degradation or other changes such as forming solvates.

The present invention reduces such problems by suspending the surface-modified nanoparticles in a dryable liquid carrier (also referred to as solvent) and then, instead of co-suspending the bulk powder by simply mixing it into the liquid, the liquid-nanoparticle suspension is sprayed onto the powder. This allows smaller amounts of the liquid to have contact with the powder, and it can be dried off relatively quickly if desired. It also does not require the same physical compatibility of the liquid with the powder (i.e. the powder does not need to be dispersible in the liquid).

The invention is applicable to any powder composition. While not subject to any specific physical characterization and not intending to be limited to any single characterization, one non-limiting way to identify a solid material as a powder is when it is composed principally of relatively small individual particles or relatively small groups of individual particles. Generally, such particles will have an average size (generally measured as an effective diameter) of less than or equal to 1,000 microns, more typically less than or equal to 200 microns. The powder material may be distinguished from the nanoparticles by relative size (i.e, the powder material comprises particles that are larger than the nanoparticles).

The dryable liquid carrier in which the surface-modified nanoparticles are suspended can be a wide range of liquids. For example, hydrocarbon solvents such as toluene, heptane, hexane, and octane may be used. Water, isopropanol, dimethyl ether, and ethanol may also be used. Propellants in liquefied form may also be used such as carbon dioxide, hydrofluorocarbons, as well as hydrocarbons such as butane. The dryable liquid may also include mixtures. The dryable liquid is selected based on suspendability and compatibility with the nanoparticles, and so that it can be conveniently dried off after spraying without leaving any unwanted residue. Liquified propellants offer an advantage of having a low boiling point, but can also be problematic if too much energy is imparted to the system when the liquid flashes off, dispersing the bulk powder to be sprayed.

The dryable liquid suspension of surface-modified nanoparticles can be sprayed by any suitable spray means, such as from a fine or course liquid spray nozzle, onto the bulk powder material. For example, a bed of bulk powder may be spread on a filter media with a suitable suction applied through the filter. This helps keep the powder in place and accelerates drying of the liquid carrier as it is applied. Also, it can be desirable to stir the powder during spraying so that the nanoparticles are applied throughout the powder composition. In one embodiment, the liquid may be sprayed without use of high pressure or atomizing air, for example, by using ultrasonic or electrospray atomization. This may be advantageous in order to avoid excessive agitation of the powder composition. Using a typical ultrasonic spray nozzle, for example, the droplets leave the nozzle with no feed velocity and their path is affected only by gravity and other ambient air conditions.

The term "nanoparticle" as used herein (unless an individual context specifically implies otherwise) will generally refer to particles, groups of particles, particulate molecules (i.e., small individual groups or loosely associated groups of molecules) and groups of particulate molecules that while potentially varied in specific geometric shape have an effective, or average, diameter that can be measured on a nanoscale (i.e., less than 100 nanometers).

The nanoparticles utilized in the invention enhance and/or maintain the flowability of the bulk powder materials within which they are present. Flowability (also called free flow) refers generally to the ability of a free-flowing material to flow steadily and consistently as individual particles or groups of individual particles such as would occur, for example, through a fine orifice. The presence of nanoparticles in the compositions of the invention also enhances floodability (also called floodable flow), which refers to the tendency of a solid or powder material toward liquid-like flow due to the material fluidization of a mass of particles by a gaseous carrier. There can be several different ways to characterize the flowability or floodability of a powder. The surface-modified nanoparticles, when present in a powder composition in accordance with the present invention, will provide an improvement in flowability and/or floodability of the powder composition when compared to the flowability and/or floodability of the bulk powder composition when substantially free of the nanoparticles. Substantially free refers essentially to the lack of the presence of a component (i.e. nanoparticles in the bulk powder composition).

Also, the inclusion of surface-modified nanoparticles allows for higher tap densities, where a larger concentration of a drug formulation may be contained in a capsule, a blister, or a reservoir-based DPI device. For example, this may contribute to more doses in a DPI device within the same sized device, rather than changing the device's shape or size. It will be understood, however, that other measurements can also be used to demonstrate improved powder flowabilities. An improvement in powder flowability can, for example, be inferred by relative improvement (i.e., compared to compositions substantially free of the nanoparticle compositions utilized in the invention) in phenomena and process parameters that are correlated with flowability. Relative improvements (i.e., reductions) in aggregation, agglomeration, attrition, flocculation, segregation, caking, bridging or in the ability to achieve uniform blends will all be understood to reflect an improvement in flowability as herein defined.

In one exemplary embodiment, a class of surface-modified nanoparticles utilized in the invention are comprised of a core material and a surface that is different (i.e., modified) from the core material. The core material may be inorganic or organic and is selected such that, as described in more detail herein, it is compatible with the powder composition with which it is combined and it is suitable for the application for which it is intended. Generally the selection of the core material will be governed at least in part by the specific performance requirements for the composition and any more general requirements for the intended application. For example, the performance requirements for the composition might require that a given core material have certain dimensional characteristics (e.g., size and shape), compatibility with the surface modifying materials along with certain stability requirements (e.g., insolubility in a processing or mixing solvent). Other requirements might be prescribed by the intended use or application of the solid composition. Such requirements might include, for example, biocompatibility or stability under more extreme environments (e.g., high temperatures).

Suitable inorganic nanoparticle core materials include calcium phosphate, hydroxy-apatite, and metal oxide nanoparticles such as zirconia, titania, silica, ceria, alumina, iron oxide, vanadia, zinc oxide, antimony oxide, tin oxide, alumina/silica, and combinations thereof. Metals such as gold, silver, or other precious metals can also be utilized as solid particles or as coatings on organic or inorganic particles.

Suitable organic nanoparticle core materials include, for example, organic polymeric nanospheres, sugars such as lactose, trehalose, glucose or sucrose, and aminoacids. In another embodiment, another class of organic polymeric nanospheres includes nanospheres that comprise polystyrene, such as those available from Bangs Laboratories, Inc. of Fishers, Ind. as powders or dispersions. Such organic polymeric nanospheres will generally have average particle sizes ranging from 20 nm to not more than 60 nm.

It will be understood that the selected nanoparticle core material may be used alone or in combination with one or more other nanoparticle core materials including mixtures and combinations of organic and inorganic nanoparticle materials. Such combinations may be uniform or have distinct phases which can be dispersed or regionally specific, e.g., layered or of a core-shell type structure. The selected nanoparticle core material, whether inorganic or organic, and in whatever form employed, will generally have an average particle diameter of less than 100 nm. In some embodiments, nanoparticles may be utilized having a smaller average effective particle diameter of, for example less than or equal to 50, 40, 30, 20, 15, 10 or 5 nm; in some embodiments from 2 nm to 20 nm; in still other embodiments from 3 nm to 10 nm. If the chosen nanoparticles or combination of nanoparticles are themselves aggregated, the maximum preferred cross-sectional dimension of the aggregated particles will be within any of these stated ranges.

In an exemplary embodiment, another class of surface-modified organic nanoparticles includes buckminsterfullerenes (fullerenes), dendrimers, branched and hyperbranched "star" polymers such as 4, 6, or 8 armed polyethylene oxide (available, for example, from Aldrich Chemical Company of Milwaukee, Wis. or Shearwater Corporation of Huntsville, Ala.) whose surface has been chemically modified. Specific examples of fullerenes include $C_{60}$, $C_{70}$, $C_{82}$, and $C_{84}$. Specific examples of dendrimers include polyamidoamine (PAMAM) dendrimers of Generations 2 through 10 (G2-G10), available also from, for example, Aldrich Chemical Company of Milwaukee, Wis.

In many cases it may be desirable for the nanoparticles utilized in the invention to be substantially spherical in shape. In other application, however, more elongated shapes may be desired. Aspect ratios less than or equal to 10 are considered preferred, with aspect ratios less than or equal to 3 generally more preferred. The core material will substantially determine the final morphology of the particle and thus a significant influence in selection of the core material may be the ability to obtain a desired size and shape in the final particle.

The surface of the selected nanoparticle core material will generally be chemically or physically modified in some manner. Both direct modification of a core surface as well as modification of a permanent or temporary shell on a core material are envisioned. Such modifications may include, for example, covalent chemical bonding, hydrogen bonding, electrostatic attraction, London forces and hydrophilic or hydrophobic interactions so long as the interaction is maintained at least during the time period required for the nanoparticles to achieve their intended utility. The surface of a nanoparticle core material may be modified with one or more surface modifying groups. The surface modifying groups may be derived from myriad surface modifying agents. Schematically, surface modifying agents may be represented by the following general formula:

$$A-B \qquad (II)$$

The A group in Formula II is a group or moiety that is capable of attaching to the surface of the nanoparticle. In those situations where the nanoparticle and/or bulk powder material is processed in solvent (which, it will be understood, can be the dryable liquid for spraying), the B group is a compatibilizing group with whatever solvent is used to process the nanoparticle and the bulk powder materials. The B group may also be a group or moiety that is capable of preventing irreversible agglomeration of the nanoparticle. It is possible for the A and B components to be the same, e.g., the attaching group may also be capable of providing the desired surface compatibility. The compatibilizing group may be reactive, but is generally non-reactive, with a component of the bulk powder phase. It is understood that the attaching composition may be comprised of more than one component or created in more than one step, e.g., the A composition may be comprised of an A' moiety which is reacted with the surface, followed by an A" moiety which can then be reacted with B. The sequence of addition is not important, i.e., the A'A"B component reactions can be wholly or partly performed prior to attachment to the core. Further description of nanoparticles in coatings can be found in Linsenbuhler, M. et. al., *Powder Technology*, 158, 2003, p. 3-20.

Many suitable classes of surface-modifying agents are known to those skilled in the art and include, for example, silanes, organic acids, organic bases and alcohols, and combinations thereof.

In another embodiment, surface-modifying agents include silanes. Examples of silanes include organosilanes such as, for example, alkylchlorosilanes, alkoxysilanes, e.g., methyltrimethoxysilane, methyltriethoxysilane, ethyltrimethoxysilane, ethyltriethoxysilane, n-propyltrimethoxysilane, n-propyltriethoxysilane, i-propyltrimethoxysilane, i-propyltriethoxysilane, butyltrimethoxysilane, butyltriethoxysilane, hexyltrimethoxysilane, octyltrimethoxysilane, 3-mercaptopropyltrimethoxysilane, n-octyltriethoxysilane, phenyltriethoxysilane, polytriethoxysilane, vinyltrimethoxysilane, vinyldimethylethoxysilane, vinylmethyldiacetoxysilane, vinylmethyldiethoxysilane, vinyltriacetoxysilane, vinyltriisopropoxysilane, vinyltrimethoxysilane, vinyltriphenoxysilane, vinyltri(t-butoxy)silane, vinyltris(isobutoxy)silane, vinyltris(isopropenoxy)silane, and vinyltris(2-methoxyethoxy)silane; trialkoxyarylsilanes; isooctyltrimethoxy-silane; N-(3-triethoxysilylpropyl) methoxyethoxyethyl carbamate; N-(3-triethoxysilylpropyl) methoxyethoxyethoxyethyl carbamate; silane functional (meth)acrylates including, e.g., 3-(methacryloyloxy)propyltrimethoxysilane, 3-acryloyloxypropyltrimethoxysilane, 3-(methacryloyloxy)propyltriethoxysilane, 3-(methacryloyloxy)propylmethyldimethoxysilane, 3-(acryloyloxypropyl)methyldimethoxysilane, 3-(methacryloyloxy)propyldimethylethoxysilane, 3-(methacryloyloxy)methyltriethoxysilane, 3-(methacryloyloxy)methyltrimethoxysilane, 3-(methacryloyloxy)propyldimethylethoxysilane, 3-(methacryloyloxy)propenyltrimethoxysilane, and 3-(methacryloyloxy)propyltrimethoxysilane; polydialkylsiloxanes including, e.g., polydimethylsiloxane, arylsilanes including, e.g., substituted and unsubstituted arylsilanes, alkylsilanes including, e.g., substituted and unsubstituted alkyl silanes including, e.g., methoxy and hydroxy substituted alkyl silanes, and combinations thereof.

Methods of surface-modifying silica using silane functional (meth)acrylates are known and are described, for example, in U.S. Pat. No. 4,491,508 (Olson et al.); U.S. Pat. No. 4,455,205 (Olson et al.); U.S. Pat. No. 4,478,876 (Chung); U.S. Pat. No. 4,486,504 (Chung); and U.S. Pat. No. 5,258,225 (Katsamberis) whose descriptions are incorporated herein by reference for such purpose. Surface-modified silica nanoparticles include silica nanoparticles surface-modified with silane surface modifying agents including, e.g., acryloyloxypropyl trimethoxysilane, 3-methacryloyloxypropyltrimethoxysilane, 3-mercaptopropyltrimethoxysilane, n-octyltrimethoxysilane, isooctyltrimethoxysilane, and combinations thereof. Silica nanoparticles can be treated with a number of surface modifying agents including, e.g., alcohols, organosilanes including, e.g., alkyltrichlorosilanes, trialkoxyarylsilanes, trialkoxy(alkyl)silanes, and combinations thereof and organotitanates and mixtures thereof.

In another embodiment, organic acid surface-modifying agents include, for example, oxyacids of carbon (e.g., carboxylic acid), sulfur and phosphorus, acid derivatized poly (ethylene) glycols (PEGs) and combinations of any of these. Suitable phosphorus containing acids include phosphonic acids including, e.g., octylphosphonic acid, laurylphosphonic acid, decylphosphonic acid, dodecylphosphonic acid, octadecylphosphonic acid, monopolyethylene glycol phosphonate and phosphates including lauryl or stearyl phosphate. Suitable sulfur containing acids include sulfates and sulfonic acids including dodecyl sulfate and lauryl sulfonate. Any such acids may be used in either acid or salt forms.

Non-silane surface modifying agents include acrylic acid, methacrylic acid, beta-carboxyethyl acrylate, mono-2-(methacryloyloxyethyl) succinate, mono(methacryloyloxypolyethyleneglycol) succinate and combinations of one or more of such agents. In another embodiment, surface-modifying agents incorporate a carboxylic acid functionality such as, for example, $CH_3O(CH_2CH_2O)_2CH_2COOH$ (hereafter MEEAA), 2-(2-methoxyethoxy)acetic acid having the chemical structure $CH_3OCH_2CH_2OCH_2COOH$ (hereafter MEAA), mono(polyethylene glycol) succinate in either acid or salt form, octanoic acid, dodecanoic acid, steric acid, acrylic and oleic acid or their acidic derivatives. In a further embodiment, surface-modified iron oxide nanoparticles include those modified with endogenous fatty acids, e.g., steric acid, or fatty acid deriviatives using endogenous compounds, e.g., steroyl lactylate or sarcosine or taurine derivatives. Further surface-modified zirconia nanoparticles include a combination of oleic acid and acrylic acid adsorbed onto the surface of the particle.

Organic base surface-modifying agents may also include alkylamines, e.g., octylamine, decylamine, dodecylamine, octadecylamine, and monopolyethylene glycol amines. Other non-silane surface modifying agents include acrylic acid, methacrylic acid, beta-carboxyethyl acrylate, mono-2-(methacryloyloxyethyl) succinate, mono(methacryloyloxypolyethyleneglycol) succinate and combinations of one or more of such agents.

Surface-modifying alcohols and thiols may also be employed including, for example, aliphatic alcohols, e.g., octadecyl, dodecyl, lauryl and furfuryl alcohol, alicyclic alcohols, e.g., cyclohexanol, and aromatic alcohols, e.g., phenol and benzyl alcohol, and combinations thereof. Thiol-based compounds are especially suitable for modifying cores with gold surfaces.

The surface-modified nanoparticles are selected in such a way that compositions formed with them are free from a degree of particle agglomeration or aggregation that would interfere with the desired properties of the composition. The surface-modified nanoparticles are generally selected to be either hydrophobic or hydrophilic such that, depending on the character of the processing solvent or the bulk material, the resulting mixture or blend exhibits substantially free flowing properties.

Suitable surface groups constituting the surface modification of the utilized nanoparticles can thus be selected based upon the nature of the processing solvents and bulk materials used and the properties desired of the resultant combination. When a processing solvent is hydrophobic, for example, one skilled in the art can select from among various hydrophobic surface groups to achieve a surface-modified particle that is compatible with the hydrophobic solvent; when the processing solvent is hydrophilic, one skilled in the art can select from various hydrophilic surface groups; and, when the solvent is a hydrofluorocarbon, one skilled in the art can select from among various compatible surface groups; and so forth. The nature of the bulk material and the desired final properties can also affect the selection of the surface composition. The nanoparticle can include two or more different surface groups (e.g., a combination of hydrophilic and hydrophobic groups) that combine to provide a nanoparticle having a desired set of characteristics. The surface groups will generally be selected to provide a statistically averaged, randomly surface-modified particle.

The surface groups will be present on the surface of the particle in an amount sufficient to provide surface-modified nanoparticles with the properties necessary for compatibility with the bulk material. In an exemplary embodiment, the surface groups are present in an amount sufficient to form a monolayer, and in another embodiment, a continuous monolayer, on the surface of at least a substantial portion of the nanoparticle.

A variety of methods are available for modifying the surfaces of nanoparticles. A surface modifying agent may, for example, be added to nanoparticles (e.g., in the form of a powder or a colloidal dispersion) and the surface modifying agent may be allowed to react with the nanoparticles. One skilled in the art will recognize that multiple synthetic sequences to bring the nanoparticle together with the compatibilizing group are possible and are envisioned within the scope of the present invention. For example, the reactive group/linker may be reacted with the nanoparticle followed by reaction with the compatibilizing group. Alternatively, the reactive group/linker may be reacted with the compatibilizing group followed by reaction with the nanoparticle. Other surface modification processes are described in, e g., U.S. Pat. No. 2,801,185 (Iler) and U.S. Pat. No. 4,522,958 (Das et al.), whose descriptions are incorporated herein by reference for such purpose.

Surface-modified nanoparticles or precursors to them may be in the form of a colloidal dispersion. Some such dispersions are commercially available as unmodified silica starting materials, for example those nano-sized colloidal silicas available under the product designations NALCO 1040, 1050, 1060, 2326, 2327, and 2329 colloidal silica from Nalco Chemical Co. of Naperville, Ill. Metal oxide colloidal dispersions include colloidal zirconium oxide, suitable examples of which are described in U.S. Pat. No. 5,037,579 (Matchett) (whose description is incorporated by reference herein), and colloidal titanium oxide, examples of which are described in U.S. Pat. No. 6,329,058 and U.S. Pat. No. 6,432,526 (Arney et al.), whose descriptions are also incorporated by reference herein. Such particles are also suitable substrates for further surface modification as described above.

The bulk powder phase (i.e., the bulk solid material) may contain any one or a mixture of particles for which a desired degree of flowability is desired. Generally the bulk phase particulate powders will have diameters less than 100 micrometers, but greater than 100 nm. In some instances, the bulk phase particulate powders may be less than 100 nm in size, but larger than the surface-modified nanoparticles. In one embodiment, the bulk phase particulate powders will have diameters ranging from 1 micrometer to 10 micrometers, and preferably from 1 micrometer to 5 micrometers. The bulk phase particulate powders may be inorganic, organic or any combination thereof. Examples of bulk phase powders include polymers; drugs; pigments; abrasives; additives; fillers such as carbon black, titanium dioxide, calcium carbonate, Feldspar and Wollastonite; excipients such as microcrystalline cellulose (and other natural or synthetic polymers), dicalcium phosphate, lactose monohydrate and other sugars; exfolients; cosmetic ingredients; and toner materials.

Surface-modified nanoparticles are present in the bulk solid materials utilized in the invention (which may comprise a mixture of one or more bulk materials) in an amount effective to enhance the flowability or floodability of the bulk material by reducing or minimizing the degree of aggregation, agglomeration or flocculation of the bulk material. The amount of surface-modified nanoparticles effective to achieve this purpose will depend, inter alia, on the composition of the bulk material, the chosen nanoparticle, the presence or absence of other adjuvants or excipients and on the particular needs and requirements of the application for which the bulk material is to be used. For example, the nature of the nanoparticle surface, the morphology of the particle and particle size may each influence the desired properties of the composition and influence the selection of a nanoparticle and the amount or concentration of nanoparticles used. The presence of as little as 0.001 percent of nanoparticles by weight of the combined composition can achieve an improvement in flowability. Generally, the nanoparticles will be present in an amount of less than or equal to 10 weight percent; in some embodiments less than or equal to 5 weight percent; less than or equal to 1 weight percent; or less than 0.1 weight percent. In some embodiments, the amount of surface-modified nanoparticles is from 0.001 to 20 percent; from 0.001 to 10 percent; from 0.01 to 5 percent; from 0.1 to 2 percent; or from 0.2 to 1 percent, by weight of the composition. In many applications it may be preferred that the selected nanoparticles be substantially spherical. The toxicology and biocompatibility of a selected nanoparticle will be particularly relevant and important for pharmaceutical applications. It will be understood that such selection and optimization of component compositions will be within the skill of those in the art who are familiar with the physical properties required for the composition in a given use or application.

In one exemplary embodiment, the surface-modified nanoparticles will not irreversibly associate with one another. The term "associate with" or "associating with" includes, for example, covalent bonding, hydrogen bonding, electrostatic attraction, London forces, and hydrophobic interactions.

One important application of the invention relates to manufacturing of drug compositions. Drugs include ingredients used for the diagnosis, treatment, cure, prevention, or mitigation of disease. Examples of drugs include but are not limited to medicaments such as antiallergics, analgesics, bronchodilators, antihistamines, therapeutic proteins and peptides, antitussives, anginal preparations, antibiotics, anti-inflammatory preparations, diuretics, hormones, or sulfonamides, such as, for example, a vasoconstrictive amine, an enzyme, an alkaloid or a steroid, and combinations of any one or more of these. Noted categories include beta-agonists, bronchodilators, anticholinergics, anti-leukotrienes, mediator release inhibitors, 5-lipoxygenase inhibitors, and phosphodiesterase inhibitors. Specific exemplary medicaments include the following: isoproterenol, phenylephrine, phenylpropanolamine, glucagon, adrenochrome, trypsin, epinephrine, ephedrine, narcotine, codeine, atropine, heparin, morphine, dihydromorphinone, dihydromorphine, ergotamine, scopolamine, methapyrilene, cyanocobalamin, terbutaline, rimiterol, salbutamol (albuterol), isoprenaline, fenoterol, oxitropium, tiotropium, reproterol, budesonide, flunisolide, ciclesonide, formoterol, fluticasone propionate, salmeterol, procaterol, ipratropium, triamcinolone acetonide, tipredane, mometasone furoate, colchicine, pirbuterol, beclomethasone, beclomethasone dipropionate, orciprenaline, fentanyl, diamorphine, and diltiazem. Others are antibiotics, such as neomycin, cephalosporins, streptomycin, penicillin, procaine penicillin, tetracycline, chlorotetracycline and hydroxytetracycline; adrenocorticotropic hormone and adrenocortical hormones, such as cortisone, hydrocortisone, hydrocortisone acetate and prednisolone; antiallergy compounds such as cromolyn sodium and nedocromil; protein and peptide molecules such as insulin, pentamidine, calcitonin, amiloride, interferon, LHRH analogues, IDNAase, heparin, and others.

If appropriate for a specific application the drug or medicaments may be used as either a free base or as one or more salts thereof. The choice of a free base or salt will be influenced by the biological impact as well as the chemical and physical stability (e.g., its tendency toward solvates, multiple polymorphs, friability, etc.) of the drug or medicament in a given formulation. Among salts of drugs and medicaments in the present invention are the following: acetate, benzenesulphonate, benzoate, bicarbonate, bitartrate, bromide, calcium edetate, camsylate, carbonate, chloride, citrate, dihydrochloride, edetate, edisylate, estolate, esylate, fumarate, fluceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylbromide, methylnitrate, methylsulphate, mucate, napsylate, nitrate, pamoate (embonate), pantothenate, phosphatediphosphate, polygalacturonate, salicylate, stearate, subacetate, succinate, sulphate, tannate, tartrate, and triethiodide.

Cationic salts of a drug or medicament may also be used. Suitable cationic salts include the alkali metals, e.g., sodium and potassium, and ammonium salts and salts of amines known in the art to be pharmaceutically acceptable, e.g., glycine, ethylene diamine, choline, diethanolamine, triethanolamine, octadecylamine, diethylamine, triethylamine, 1-amino-2-propanol, 2-amino-2-(hydroxymethyl)propane-1,3-diol and 1-(3,4-dihydroxyphenyl)-2 isopropylaminoethanol.

For pharmaceutical purposes, the particle size of a drug or medicament powder will generally be no greater than 100 micrometers in diameter. In other embodiments, the particle size will be less than 25 micrometers in diameter. Desirably, the particle size of the finely-divided solid powder should for physiological reasons be less than 25 micrometers in diameter and in other embodiments, less than 10 micrometers in diameter, and in other embodiments, less than 5 micrometers.

Pharmaceutical formulations frequently will consist of blends of one or more drugs or medicaments with one or more excipients that are used as intermediate materials (isolated or in-process) before the final product is manufactured. Suitable excipients are listed in the Handbook of Pharmaceutical Excipients (Rowe, et al., APhA Publications, 2003) and are exemplified by microcrystalline cellulose, dicalcium phosphate, lactose monohydrate, mannose, sorbitol, calcium carbonate, starches and magnesium or zinc stearates. The surface-modified nanoparticles may have many potential benefits in the preparation of these excipients/drug blends, including reducing mixing times, reducing attrition during processing and improving the homogeneity of the blend.

In another use, a pharmaceutical inhalation powder formulation will consist of a medicament, an optional excipient, and surface-modified nanoparticles. It may be desirable for the medicament particles to be less than 10 micrometers in size such that they can be inhaled into the lung of a patient. The optional excipient may consist of a sugar, such as lactose monohydrate, and may have particle sizes substantially larger than 10 microns. The surface-modified nanoparticles may be configured in such a way that they are arranged on the surface of the medicament and/or optional excipient particles. In one embodiment, the surface-modified nanoparticles may be primarily contained on the surface of large excipient particles, such that when the patient inhales the formulation, a substantial fraction of the respirable medicament particles deposit in the patient's lung, whereas the large excipient particles, and the nanoparticles on the surface of the large excipient particles collect in the patient's mouth and throat. In this way, the amount of nanoparticles reaching the patient's lung may be minimized.

In another embodiment, the dry power inhalers may have the powder stored in a storage device prior to dosing. This storage device may comprise a reservoir, capsule, blister, or dimpled tape. In an exemplary embodiment, the drug powder used in the formulation is a micronized crystalline powder, but may also be an amorphous powder from a process such as spray drying. Additionally, the drug may be contained in particles that are a matrix of drug and some excipient. The DPI may be a multi-dose device or may be a single dose device.

In a further embodiment, the pharmaceutical powder formulation may be used for nasal drug delivery.

The compositions produced by the process of the invention will find utility in any application where an increase or improvement in flow properties of a powder material is desired. Some specific applications, including some outside pharmaceutical applications, for the compositions and methods of the invention include:

(a) In the weighing, metering and mixing of powders where accurate measurements and or increased homogeneities are required;
(b) In any application where an increase in powder "tap density" (decreased volume per unit mass) is desired, including as an aid to the shipment or storage of bulk materials in powder form;
(c) In the preparation of solid ink jet or printing inks and toners;
(d) In the preparation, handling and mixing of paint pigments;
(e) To increase graphite densities in battery anodes;
(f) To decrease the amount of energy required to mix or blend powders;
(g) To prepare passive dry powder inhalers, wherein the inhaler relies on the patient's inspiratory airflow to aerosolize and/or deagglomerate the powder;
(h) To prepare dry powder inhaler (DPI) devices with one or more pharmaceutically active materials. DPI devices contain a mouthpiece and a powder containment system. Compositions of the invention that comprise a bulk solid material (that includes one or more pharmaceutically active ingredients) and nanoparticles may be placed in the powder containment system;
(i) To improve the accuracy and/or homogeneity of pharmaceutical compositions that are filled into capsules or formed into tablets; and
(j) To prepare high tap density powders for use in rapid dissolve tablets, such as described in U.S. Pat. No. 6,051,252 (Liebowitz et al.), herein incorporated by reference.

EXAMPLES

The following examples are offered to aid in the understanding of the present invention and are not to be construed as limiting the scope thereof. Unless otherwise indicated, all parts and percentages are by weight.

Hydrophilic Surface-Modified Zinc Oxide Nanoparticle Preparation A

Zinc lactate dihydrate (Pfaltz & Bauer, Waterbury, Conn.) was sieved through a 1 mm stainless steel mesh. Any particles too large to go through the mesh were ground in a mortar and pestle until they could pass through the mesh. The resulting powder was then dried in a vacuum oven overnight at 100° C. Thermal gravimetric analysis (ramp to 120° C. at 20° C. per minute and hold for 20 minutes) indicated that the sample contained 0.9% by weight water.

Dimethyl sulfoxide (DMSO, 500 g, EMD Chemicals, Gibbstown, N.J., OMNISOLV grade) was placed in a 2 liter, 3 neck round-bottomed flask. With mechanical stirring, zinc acetate (68.26 g, 0.372 mole, Alfa Aesar, Ward Hill, Mass.) and the vacuum-dried zinc lactate (90.58 g, 0.372 mole) were added as powders to the flask via a powder addition funnel. DMSO (77.3 g) was used to wash residual zinc acetate or zinc lactate remaining on the powder addition funnel into the round-bottomed flask. The flask was placed in a silicone oil bath, heated such that the temperature of the reactants in the flask was 84° C. After the powders were dissolved, water (2.81 mL, 0.156 mole, EMD Chemicals, Gibbstown, N.J., OMNISOLV grade) was added. After several minutes of additional stirring, 25 percent tetramethylammonium hydroxide in methanol (461 g, 1.265 mole, Alfa Aesar, Ward Hill, Mass.) was added to the flask in a steady stream over 15 minutes via a reparatory funnel.

The size of the resulting zinc oxide nanoparticles was monitored using UV-visible spectroscopy (as described in U.S. Provisional Patent Filing Ser. No. 61/016,048) by taking 0.1 mL aliquots of the resulting mixture and diluting them with 23.74 g ethanol. Size measurements were performed hourly until a size of 5.1 nm was reached after three hours of reaction time. The round-bottomed flask was then removed from the oil bath.

The methanol and DMSO were stripped via rotary evaporation, first using a water aspirator to provide a vacuum for stripping the methanol, then using a mechanical pump to provide a vacuum for stripping the DMSO. The resulting solids were re-dispersed in 876 g 2-propanol (EMD Chemicals, Gibbstown, N.J., OMNISOLV grade) to provide a hazy dispersion. Gas chromatography (GC) was used to analyze the resulting ZnO dispersion and showed that there was between 2.6 and 3.2% DMSO remaining in the dispersion.

To the resulting cooled mixture was added 59.8 g of 3-(ethylenediamino)propyl-functionalized silica gel (Sigma-Aldrich Chemical Company, St. Louis, Mo.), and the resulting mixture was stirred for 24 hours. The resulting slurry was filtered through a bed of Celite™ 521 diatomaceous earth filter agent (Sigma-Aldrich Chemical Company, St. Louis, Mo.) supported on an ASTM C glass frit funnel filter. The bed of Celite™ 521 diatomaceous earth filter agent and silica gel was rinsed with four portions of 2-propanol, totaling 1800 mL. The dispersion was filtered through a 1 micron glass fiber membrane syringe filter (Acrodisc™, Pall Life Sciences, East Hills, N.Y.).

The ZnO dispersion in 2-propanol was further purified through tangential flow filtration (TFF) using a KROSFLO Research II TFF System (Spectrum Labs, Rancho Dominguez, Calif.). The dispersion was concentrated to 950 mL on the TFF system using a hollow fiber filter module (Spectrum Labs, Rancho Dominguez, Calif., P/N M25S-100-01N, 1050 cm$^2$ filter area, 50 kilodalton cutoff). The flow rate of the peristaltic pump of the TFF system was set to 1700 mL per minute. Using the same module, the dispersion was washed with 4750 mL (five volumes) of 2-propanol with the TFF system in diafiltration mode (2-propanol lost through the membrane was replaced with fresh 2-propanol).

UV-visible spectroscopy was used to measure the particle size and it was determined to be 5.1 nm. The height of the absorption edge in the resulting spectrum was measured as described in U.S. Provision application Ser. No. 61/016,048, and a zinc oxide concentration of 49 mg/mL was calculated. With a final dispersion volume of 930 mL, this yielded 46 g of zinc oxide nanoparticles (not including weight of ligand).

Hydrophilic Surface-Modified Zinc Oxide Nanoparticle Dispersion B

Zinc lactate dihydrate (Pfaltz & Bauer, Waterbury, Conn.) was sieved through a 1 mm stainless steel mesh. Any particles too large to go through the mesh were ground in a mortar and pestle until they could pass through the mesh. The resulting powder was then dried in a vacuum oven overnight at 100° C. Thermal gravimetric analysis (ramp to 120° C. at 20° C. per minute and hold for 20 minutes) indicated that the sample contained 0.7% by weight water.

Dimethyl sulfoxide (DMSO, 200 mL, EMD Chemicals, Gibbstown, N.J., OMNISOLV grade) was placed in a 1 liter, 3 neck round-bottomed flask. With mechanical stirring, zinc acetate (28.44 g, 0.155 mole, Alfa Aesar, Ward Hill, Mass.) and the vacuum-dried zinc lactate (37.74 g, 0.155 mole) were added as powders to the flask via a powder addition funnel. DMSO (40 mL) was used to wash residual zinc acetate or zinc lactate remaining on the powder addition funnel into the round-bottomed flask. The flask was placed in a silicone oil bath, heated such that the temperature of the reactants in the flask was 75° C. After several minutes of additional stirring, 25 percent tetramethylammonium hydroxide in methanol (192.1 g, 0.527 mole, Alfa Aesar, Ward Hill, Mass.) was added to the flask in a steady stream over 15 minutes via a separatory funnel.

The size of the resulting zinc oxide nanoparticles was monitored using UV-visible spectroscopy (as described above) by taking 0.1 mL aliquots of the resulting mixture and diluting them with an amount of 200 proof (or pure) ethanol (USP grade, Aaper Alcohol and Chemical Co., Shelbyville, Ky.) between 23.82 and 23.92 g. Size measurements were performed hourly until a size of 5.0 nm was reached after six hours of reaction time. The round-bottomed flask was then removed from the oil bath.

The methanol and DMSO were stripped via rotary evaporation, first using a water aspirator to provide a vacuum for stripping the methanol, then using a mechanical pump to provide a vacuum for stripping the DMSO. The resulting solids were re-dispersed in 360 g 200 proof (or pure) ethanol to provide a hazy dispersion.

To one half of the resulting cooled mixture was added 11.6 g of 3-(ethylenediamino)propyl-functionalized silica gel (Sigma-Aldrich Chemical Company, St. Louis, Mo.), and the resulting mixture was stirred for 3 days. The resulting slurry was filtered through a bed of Celite™ 521 diatomaceous earth filter agent (Sigma-Aldrich Chemical Company, St. Louis, Mo.) supported on an ASTM C glass frit funnel filter. The bed of Celite™ 521 diatomaceous earth filter agent and silica gel was rinsed with four portions of 200 proof (or pure) ethanol, totaling 400 mL. The dispersion was filtered through a 1 micron glass fiber membrane syringe filter (Acrodisc™, Pall Life Sciences, East Hills, N.Y.).

The ZnO dispersion in ethanol was further purified through tangential flow filtration (TFF) using a KROSFLO Research II TFF System (Spectrum Labs, Rancho Dominguez, Calif.). The dispersion was concentrated to 156 mL on the TFF system using a hollow fiber filter module (Spectrum Labs, Rancho Dominguez, Calif., P/N X215-300-02N, 145 cm$^2$ filter area, 10 kilodalton cutoff). The flow rate of the peristaltic pump of the TFF system was set to 400 mL per minute. Using the same module, the dispersion was washed with 780 mL (five volumes) of 200 proof (or pure) ethanol with the TFF system in diafiltration mode (ethanol lost through the membrane was replaced with fresh ethanol).

The ethanol dispersion of zinc oxide nanoparticles was solvent exchanged into 2-propanol by taking 65 mL of the ethanol dispersion and adding to it 69 mL of 2-propanol. The dispersion was then rotary evaporated to a volume of 65 mL. This process was repeated for a total of five times, resulting in a dispersion of zinc oxide nanoparticles in 2-propanol.

UV-visible spectroscopy was used to measure the particle size and it was determined to be 5.0 nm. The height of the absorption edge in the resulting spectrum was measured as described above, and a zinc oxide concentration of 51 mg/mL was calculated.

Example 1

A micronized alpha-lactose monohydrate powder (referred to below as "lactose") was treated with surface modified nanoparticles as follows.

Approximately 5 grams of micronized lactose (average particle size approximately 2 micron) was put into a Buchner funnel fitted with a hardened paper filter (Whatman grade 50). A vacuum was pulled through the funnel to draw suction through the powder bed. The hydrophilic surface-modified zinc oxide nanoparticle dispersion B was diluted with 2-propanol to a concentration of 10 mg/mL. Approximately 20 mL of the diluted dispersion was placed into a 60 mL syringe that was fitted to a syringe pump. The nanoparticle dispersion was fed by the syringe pump at a rate of 1 mL/min to an ultrasonic nozzle (Sono-Tek Co., Milton, N.Y.) that was used to atomize the nanoparticle dispersion. The ultrasonic nozzle was operated at 120 kHz with a power setting of 1.8 Watts. The ultrasonic nozzle was oriented perpendicular to the filter and aligned approximately 1 cm above the top wall of the Buchner funnel. The dispersion was sprayed for 10 minutes onto the powder bed while continually stirring the powder to exposed fresh lactose surfaces for coating, thus giving a nominal surface-modified nanoparticle concentration of 2% by weight in the treated powder. After the spraying was complete, the vacuum was allowed to continue for approximately 5 minutes to further evaporate any residual solvent. The treated powder was then sieved through a 140 mesh sieve.

The resulting powder was free flowing. Examination of the lactose particles by scanning electron microscopy showed no change in the particle morphology for the lactose that had been sprayed with the surface-modified nanoparticles.

As a comparison, a blend of the same lactose and surface-modified nanoparticle above was prepared according to a procedure similar to that described in Example 21 of International Publication No. WO 2007/019229 with the exception that the surface-modified nanoparticles were initially suspended in isopropanol instead of heptane. In brief, the lactose and nanoparticle were both suspended in isopropanol, mixed for approximately 30 minutes to create a thoroughly blended dispersion, and then dried in a rotary evaporator. The resulting powder was highly agglomerated and did not flow freely. On further examination it was determined that the lactose particles had recrystallized to form needle-shaped crystals with aspect ratios as high as 10, whereas the original lactose particles, although irregular, are roughly spherical in shape and most typically have an aspect ratio between 1 and 2.

Example 2

A treated lactose powder was prepared according to the general procedure of Example 1.

Approximately 15 grams of the micronized lactose (average particle size approximately 2 micron) was put into a Buchner funnel fitted with a hardened paper filter (Whatman grade 50). A vacuum was pulled through the funnel to draw suction through the powder bed. Approximately 30 mL of the nanoparticle dispersion of preparation A was placed into a 60 mL syringe that was fitted to a syringe pump. The nanoparticle dispersion was fed by the syringe pump at a rate of 1.2 mL/min to an ultrasonic nozzle (Sono-Tek Co., Milton, N.Y.) that was used to atomize the nanoparticle dispersion. The ultrasonic nozzle was operated at 120 kHz with a power setting of 1.8 Watts. The ultrasonic nozzle was oriented perpendicular to the filter and aligned approximately 1 cm above the top wall of the Buchner funnel. The dispersion was sprayed for 20 minutes onto the powder bed while continually stirring the powder to exposed fresh lactose surfaces for coating, thus giving a nominal surface-modified nanoparticle concentration of 8% by weight in the treated powder. After the spraying was complete, the vacuum was allowed to continue for approximately 5 minutes to further evaporate any residual solvent. The funnel with powder was then further dried in a vacuum oven for an additional 15 minutes at approximately 45° C. The treated powder was then sieved through a 140 mesh sieve.

The resulting powder was free flowing. Examination of the lactose particles by scanning electron microscopy showed no change in the particle morphology for the lactose that had been sprayed with the surface-modified nanoparticles.

Further examination by X-ray scattering was performed to observe if there was any change in the crystalline character of the lactose particles after being sprayed with the surface-modified nanoparticles. Samples were placed on a zero background specimen holder composed of single crystal quartz. Reflection geometry data were collected in the form of a survey scan by use of a Philips vertical diffractometer, copper $K_\alpha$ radiation, and proportional detector registry of the scattered radiation. The diffractometer was fitted with variable incident beam slits, fixed diffracted beam slits, and graphite diffracted beam monochromator. The survey scan was conducted from 5 to 55 degrees (2θ) using a 0.04 degree step size and 6 second dwell time. X-ray generator settings of 45 kV and 35 mA were employed. The lactose powder before spraying (untreated) and the lactose powder sprayed with surface-modified nanoparticles (treated) produced essentially identical diffraction patterns, thus indicating no change in crystallinity.

The lactose particle size was measured by light scattering (Mastersizer 2000, Malvern Instruments) before and after spraying with the surface-modified nanoparticles. A dilute suspension with a concentration of 4 mg/mL of powder was suspended in 0.7% sorbitan trioleate (Span® 85) in heptane and sonicated to ensure that the suspension was homogeneous. Results were reported as the average particle size, D50%. The lactose particle size measured before and after the spraying process was essentially unchanged (2.05 micron and 2.17 micron, respectively)

The ability of the powder to be aerosolized was measured using an inertial cascade impactor as follows. A small amount (nominally 2 mg) of powder was weighed into a size three Shionogi Quali-V® hydroxypropyl methylcellulose capsule (Shionogi Qualicaps, Madrid, Spain) and loaded into an Aerolizer® device ("DPI" device, commercially available as a Foradil® Aerolizer® product, available from Schering Plough Co.), which was tested for pharmaceutical performance using a Next Generation Pharmaceutical Impactor ("NGI") (MSP Corporation, Shoreview, Minn.). Samples of micronized lactose powder were tested in addition to testing samples of the nanoparticle modified lactose powder. The NGI was coupled with a USP throat (United States Pharmacopeia, USP 24 <601> Aerosols, Metered Dose Inhalers, and Dry Powder Inhalers, FIG. 4) and operated at a volumetric flow rate of 60 lpm for a collection time of four seconds. A suitable coupler was affixed to the USP throat to provide an air-tight seal between the DPI device and the throat. For all testing, the stage cups of the NGI were coated with a surfactant to prevent particle bounce and re-entrainment. The amount of lactose collected on each component of the NGI testing apparatus was determined by rinsing the component with a measured volume of an appropriate solvent and subjecting the rinsed material to HPLC analysis with charged aerosol detection to determine lactose concentration. Data that was returned from HPLC analysis was analyzed to determine the average amount of drug collected on the DPI and capsule, the USP throat, and on each component of the NGI per delivered dose.

Using the individual component values, the respirable fraction and delivery efficiency were calculated for each powder sample. Respirable mass is defined as the total delivered dose that is measured to be smaller than the respirable limit of 4.5 micrometers in aerodynamic diameter. Respirable fraction is defined as the percentage of a delivered dose that reaches the entry of the throat and is smaller than the respirable limit. Delivery efficiency is defined as the respirable mass divided by the total delivered dose. When using the NGI, respirable mass is collected in cups 3, 4, 5, 6, and 7, and on the filter. Mass collected in the throat and cups 1 and 2 are considered non-respirable. The measured respirable fraction of the nanoparticle modified lactose powder was 56%, and the delivery efficiency of the nanoparticle modified lactose powder was 42%.

Various modifications and alterations of this invention will be apparent to those skilled in the art without departing from the scope and spirit of this invention, and it should be understood that this invention is not limited to the illustrative embodiments set forth herein.

We claim:

1. A process for manufacturing a powder drug composition, comprising:
   preparing a suspension of surface-modified nanoparticles having an average particle size diameter of less than 100 nm in a dryable liquid carrier;
   spraying the dryable liquid carrier containing the surface-modified nanoparticles onto particles of a powder ingredient of a drug composition;
   evaporating off the dryable liquid carrier so as to leave the surface-modified nanoparticles on the powder ingredient without the dryable liquid carrier; and
   optionally adding other ingredients of the powder drug composition.

2. The process of claim 1, wherein the surface-modified nanoparticles have a hydrophilic surface modification.

3. The process of claim 1, wherein the surface-modified nanoparticles have a hydrophobic surface modification.

4. The process of claim 1, wherein the surface-modified nanoparticles comprise nanoparticles having a surface modification selected from one of at least two different surface modifications, wherein at least one surface modification is hydrophilic and at least one surface modification is hydrophobic.

5. The process claim 1, wherein the nanoparticles have a core material selected from the group consisting of silicas, calcium phosphates, iron oxides, zinc oxides, zirconia and alumina compounds.

6. The process of claim 1, wherein the average diameter of the surface-modified nanoparticles is less than 20 nm.

7. The process of claim 1, wherein the dryable liquid carrier is selected from the group consisting of water, isopropyl alcohol, ethanol, dimethyl ether, heptane, toluene, liquefied carbon dioxide, liquefied hydrocarbon, liquefied hydrofluorocarbon, and mixtures thereof.

8. The process of claim 7, wherein the dryable liquid carrier is isopropyl alcohol.

9. The process of claim 7, wherein the dryable liquid carrier is heptane.

10. The process of claim 1, wherein the particles of the powder drug composition have a median particle size diameter less than 200 micrometers.

11. The process of claim 1, wherein the powder drug composition is a powdered medicament formulation.

12. The process of claim 1, wherein the powder ingredient comprises lactose.

13. The process of claim 11, wherein the powdered medicament formulation is a dry powder inhaler formulation.

14. The process of claim 1, wherein the particles of the powder ingredient are stirred as the dryable liquid carrier containing surface-modified nanoparticles is sprayed onto the particles of the powder ingredient.

15. The process of claim 1, wherein the liquid carrier is removed by vacuum filtration, spray drying, rotary evaporation, bulk evaporation or freeze drying.

16. The process of claim 1, wherein the particles of the powder ingredient form a bed of particles on a filtration media through which a suction is applied to the bed of particles.

17. The process of claim 1, wherein the particles of the powder ingredient are airborne when the dryable liquid carrier containing nanoparticles is sprayed onto the surface of the powder ingredient.

18. The process of claim 17, wherein the particles of the powder ingredient are contained in one airflow that impinges upon a second airflow containing droplets of the dryable liquid carrier containing nanoparticles.

* * * * *